US012808854B2

(12) United States Patent
Warner et al.

(10) Patent No.: US 12,808,854 B2
(45) Date of Patent: Nov. 24, 2026

(54) REPLACEABLE MODULE FOR A GAS DETECTOR

(71) Applicant: Carrier Corporation, Palm Beach Gardens, FL (US)

(72) Inventors: Tanner Warner, Chanhassen, MN (US); Glen Edwards, Burnsville, MN (US)

(73) Assignee: DETECTOR ELECTRONICS BUYER US, LLC, Stamford, CT (US)

( * ) Notice: Subject to any disclaimer, the term of this patent is extended or adjusted under 35 U.S.C. 154(b) by 296 days.

(21) Appl. No.: 18/624,090

(22) Filed: Apr. 1, 2024

(65) Prior Publication Data

US 2024/0337640 A1 Oct. 10, 2024

Related U.S. Application Data

(60) Provisional application No. 63/494,803, filed on Apr. 7, 2023.

(51) Int. Cl.
*G01N 33/00* (2006.01)
*G01D 11/24* (2006.01)

(52) U.S. Cl.
CPC ................................ *G01N 33/0027* (2013.01)

(58) Field of Classification Search
CPC ..... G01N 33/00; G01N 33/0027; G01D 11/24
See application file for complete search history.

(56) References Cited

U.S. PATENT DOCUMENTS

| | | | | |
|---|---|---|---|---|
| 5,103,216 A * | 4/1992 | Sisselman | G08B 29/181 | 116/315 |
| 5,596,314 A * | 1/1997 | Goldstein | H01M 50/213 | 429/96 |
| 7,089,778 B2 * | 8/2006 | Rabenecker | G01N 33/0009 | 73/23.2 |
| 7,414,538 B2 * | 8/2008 | Cook | G08B 17/10 | 340/693.11 |
| 2004/0209507 A1 * | 10/2004 | Starta | H01R 13/71 | 439/247 |
| 2013/0327121 A1 | 12/2013 | Shimazaki et al. | | |
| 2018/0085696 A1 | 3/2018 | Morris et al. | | |

FOREIGN PATENT DOCUMENTS

| | | | |
|---|---|---|---|
| DE | 102021210581 A1 | 3/2023 | |
| GB | 2403550 A * | 1/2005 | G01N 33/0009 |

OTHER PUBLICATIONS

European Search Report for Application No. 24168853, Issued Jul. 18, 2024, 8 Pages.

* cited by examiner

*Primary Examiner* — Nguyen Q. Ha
(74) *Attorney, Agent, or Firm* — CANTOR COLBURN LLP

(57) ABSTRACT

Embodiments of the disclosure describe a replaceable module for a gas detector. The replaceable module may include a sensor housing and a cover. The sensor housing is adapted to accommodate a sensor and a first sensor circuit of the gas detector. The sensor is detachably connected to the first sensor circuit. The cover is detachably connected to the sensor housing. The cover may include at least one resilient engaging member extending from the cover and defines at least one protrusion adapted to engage with a lower enclosure of the gas detector to restrict a movement of the cover relative to the lower enclosure.

18 Claims, 10 Drawing Sheets

REPLACEABLE MODULE FOR A GAS DETECTOR

CROSS REFERENCE TO RELATED APPLICATION

This application claims the benefit of U.S. Provisional Patent Application No. 63/494,803 filed on Apr. 7, 2023, which is incorporated by reference herein in its entirety.

FIELD OF THE INVENTION

The disclosure generally relates to gas detectors. More particularly, the disclosure relates to a replaceable module for a gas detector.

BACKGROUND

Gas detectors are widely used to detect the presence of dangerous or toxic gases such as carbon monoxide, hydrogen sulfide, and others, in industrial, commercial, and residential areas. Typically, a gas detector may include a consumable sensor module removably installed in an enclosure of the gas detector for housing a sensor. In case of malfunctioning of the sensor of the gas detector, the consumable sensor module may be replaced or removed from the gas detector periodically for repair. Alternatively, in case the consumable sensor module reaches the end of an operational life, the consumable sensor module may be replaced.

However, despite their utility, existing consumable sensor modules are not without disadvantages. Currently, the consumable sensor module is installed in the enclosure of the gas detector using mechanical fasteners and one or more tools, to retain the consumable sensor module within the enclosure. However, implementation of mechanical fasteners and one or more tools in the installation of the consumable sensor module is a cumbersome process, as this consumes additional time and effort. This increases the time consumption in the overall servicing or maintenance of the consumable sensor module, which further increases the overall cost associated with the installation and/or replacement of the consumable sensor module.

Moreover, the existing consumable sensor modules are designed to prevent the entry of foreign particles, including dust and water, in the gas detector. In the existing consumable sensor modules, several sealing provisions are used to achieve a sealing connection. However, such sealing provisions not only increase the number of components but also introduce additional inspection steps during the assembly of the consumable sensor module.

Therefore, a module for a gas detector that overcomes one or more above-mentioned limitations associated with the existing consumable sensor module, is desirable.

SUMMARY

This summary is provided to introduce a selection of concepts, in a simplified format, that are further described in the detailed description of the disclosure. This summary is neither intended to identify key or essential inventive concepts of the disclosure and nor is it intended for determining the scope of the disclosure.

Disclosed herein is a replaceable module for a gas detector. The replaceable module may include a sensor housing and a cover. The sensor housing is adapted to accommodate a sensor and a first sensor circuit of the gas detector. The sensor is detachably connected to the first sensor circuit. The cover is detachably connected to the sensor housing. The cover may include at least one resilient engaging member extending from the cover. Moreover, the cover defines at least one protrusion adapted to engage with a lower enclosure of the gas detector to restrict a movement of the cover relative to the lower enclosure.

In one or more embodiments, the sensor housing and the cover detachably connected to the sensor housing are collectively adapted to be snap fit in the lower enclosure of the gas detector.

In one or more embodiments, the at least one protrusion is extended in a parallel orientation relative to the cover. The at least one protrusion is adapted to engage with an internal peripheral surface of the lower enclosure to restrict an upward movement of the replaceable module from the lower enclosure.

In one or more embodiments, the at least one protrusion is adapted to be engaged with a mounting portion formed on the internal peripheral surface of the lower enclosure.

In one or more embodiments, the at least one resilient engaging member is adapted to be pressed to disengage the at least one protrusion from the lower enclosure to remove the replaceable module from the lower enclosure.

In one or more embodiments, the at least one resilient engaging member is extended in an orthogonal orientation relative to the cover. The at least one resilient engaging member is adapted to be pressed towards a center of the cover to disengage the at least one protrusion from the internal peripheral surface of the lower enclosure to remove the replaceable module from the lower enclosure.

In one or more embodiments, the sensor housing may include a side wall defining at least one cut-out adapted to at least partially accommodate the at least one resilient engaging member, when the cover is detachably coupled to the sensor housing.

In one or more embodiments, the at least one resilient engaging member is vertically extended from the cover to provide a gripping area for inwardly pressing the at least one resilient engaging member.

In one or more embodiments, the first sensor circuit is installed in the sensor housing positioned in the lower enclosure and is adapted to form an electrical connection with a second sensor circuit of an upper enclosure of the gas detector adapted to be engaged with the lower enclosure.

In one or more embodiments, the sensor housing may include a protruding member adapted to interlock with a receiving member of the upper enclosure to restrict the rotation of the replaceable module with the lower enclosure.

In one or more embodiments, the cover is disposed in the sensor housing to hold the first sensor circuit in a recess defined within the sensor housing.

In one or more embodiments, the cover may include a plurality of snaps positioned in proximity to the side wall of the sensor housing. The plurality of snaps is adapted to be pressed towards a center of the replaceable module to remove the replaceable module from the lower enclosure.

In one or more embodiments, the PCB is supported in the cover. The PCB is adapted to form the electrical connection with the second sensor circuit positioned in the upper enclosure.

In one or more embodiments, each of the sensor housing and the cover is formed of at least one of a polymeric material and an elastomeric material.

Disclosed herein is a method of replacing a replaceable module of a gas detector. The method may include adjusting at least one resilient engaging member of the replaceable module to disengage at least one protrusion of the at least one resilient engaging member from an internal peripheral surface of a lower enclosure of the gas detector. Further, the method may include lifting the disengaged replaceable module by gripping the at least one resilient engaging member to remove the replaceable module from the lower enclosure.

In one or more embodiments, adjusting the at least one resilient engaging member may include pressing the at least one resilient engaging member inwardly to disengage the at least one protrusion from a mounting portion of the internal peripheral surface.

Further, a replaceable module, disclosed herein, may include a sensor housing and a cover detachably connected to the sensor housing. The sensor housing is adapted to accommodate a sensor and a first sensor circuit of the gas detector. The sensor is detachably connected to the first sensor circuit. The sensor housing may include a side wall and a sealing member protruding from the side wall. The sealing member is adapted to form a sealing surface in contact with an internal peripheral surface of the lower enclosure. The cover may include at least one resilient engaging member extending from the cover. Moreover, the cover defines at least one protrusion adapted to engage with a lower enclosure of the gas detector, such that the at least one resilient engaging member is adapted to be pressed to disengage the at least one protrusion from the lower enclosure to remove the replaceable module.

In one or more embodiments, the sensor housing and the cover detachably connected to the sensor housing are collectively adapted to be snap fit in the lower enclosure of the gas detector.

In one or more embodiments, the sealing member is adapted to form an interference fit with the internal peripheral surface of the lower enclosure to form the sealing surface with the lower enclosure.

In one or more embodiments, the sealing member is integrated with the sensor housing of the replaceable module. The sensor housing and the sealing member are integrally formed.

To further clarify the advantages and features of the methods, systems, and apparatuses, a more particular description of the methods, systems, and apparatuses will be rendered by reference to specific embodiments thereof, which are illustrated in the appended drawings. It is appreciated that these drawings depict only typical embodiments of the disclosure and are therefore not to be considered limiting of its scope. The disclosure will be described and explained with additional specificity and detail with the accompanying drawings.

BRIEF DESCRIPTION OF THE DRAWINGS

These and other features, aspects, and advantages of the disclosure will become better understood when the following detailed description is read with reference to the accompanying drawings in which like characters represent like parts throughout the drawings, wherein.

Figure 1:
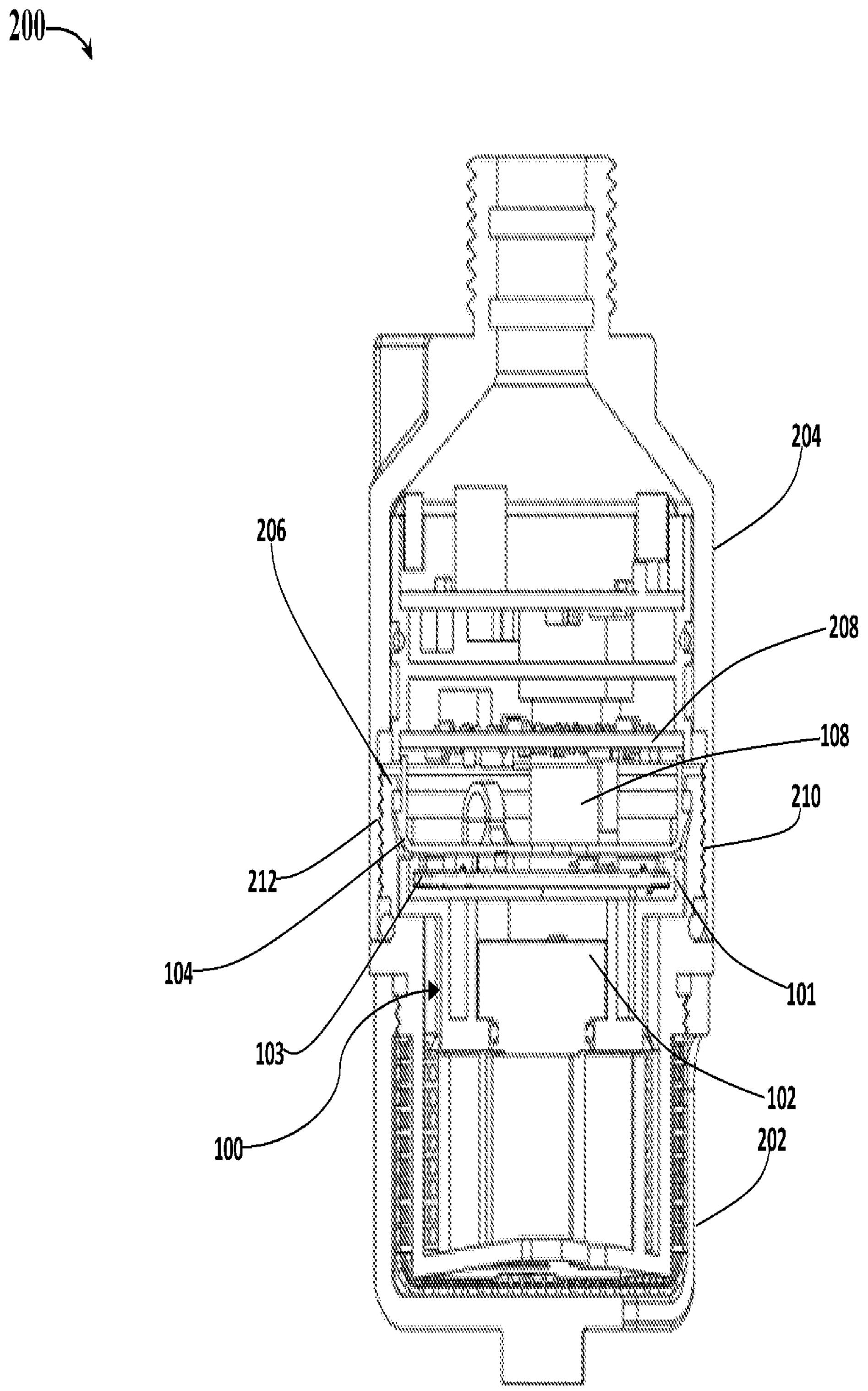
FIG. 1 exemplarily illustrates a cross-sectional view of a gas detector, according to one or more embodiments of the disclosure.

Further, skilled artisans will appreciate that elements in the drawings are illustrated for simplicity and may not have necessarily been drawn to scale. For example, the flow charts illustrate the method in terms of the most prominent steps involved to help to improve understanding of aspects of the disclosure. Furthermore, in terms of the construction of the device, one or more components of the device may have been represented in the drawings by conventional symbols, and the drawings may show only those specific details that are pertinent to understanding the embodiments of the disclosure so as not to obscure the drawings with details that will be readily apparent to those of ordinary skill in the art having the benefit of the description herein.

DETAILED DESCRIPTION

For the purpose of promoting an understanding of the principles of the disclosure, reference will now be made to the various embodiments and specific language will be used to describe the same. It will nevertheless be understood that no limitation of the scope of the disclosure is thereby intended, such alterations and further modifications in the illustrated system, and such further applications of the principles of the disclosure as illustrated therein being contemplated as would normally occur to one skilled in the art to which the disclosure relates.

It will be understood by those skilled in the art that the foregoing general description and the following detailed description are explanatory of the disclosure and are not intended to be restrictive thereof.

Reference throughout this specification to "an aspect", "another aspect" or similar language means that a particular feature, structure, or characteristic described in connection with the embodiment is included in at least one embodiment of the disclosure. Thus, appearances of the phrase "in an embodiment", "in another embodiment", "some embodiments", "one or more embodiments" and similar language throughout this specification may, but do not necessarily, all refer to the same embodiment.

The terms "comprises", "comprising", or any other variations thereof, are intended to cover a non-exclusive inclusion, such that a process or method that comprises a list of steps does not include only those steps but may include other steps not expressly listed or inherent to such process or method. Similarly, one or more devices or sub-systems or elements or structures or components proceeded by "comprises . . . a" does not, without more constraints, preclude the existence of other devices or other sub-systems or other elements or other structures or other components or additional devices or additional sub-systems or additional elements or additional structures or additional components.

Embodiments of the disclosure will be described below in detail with reference to the accompanying drawings.

Figure 2:
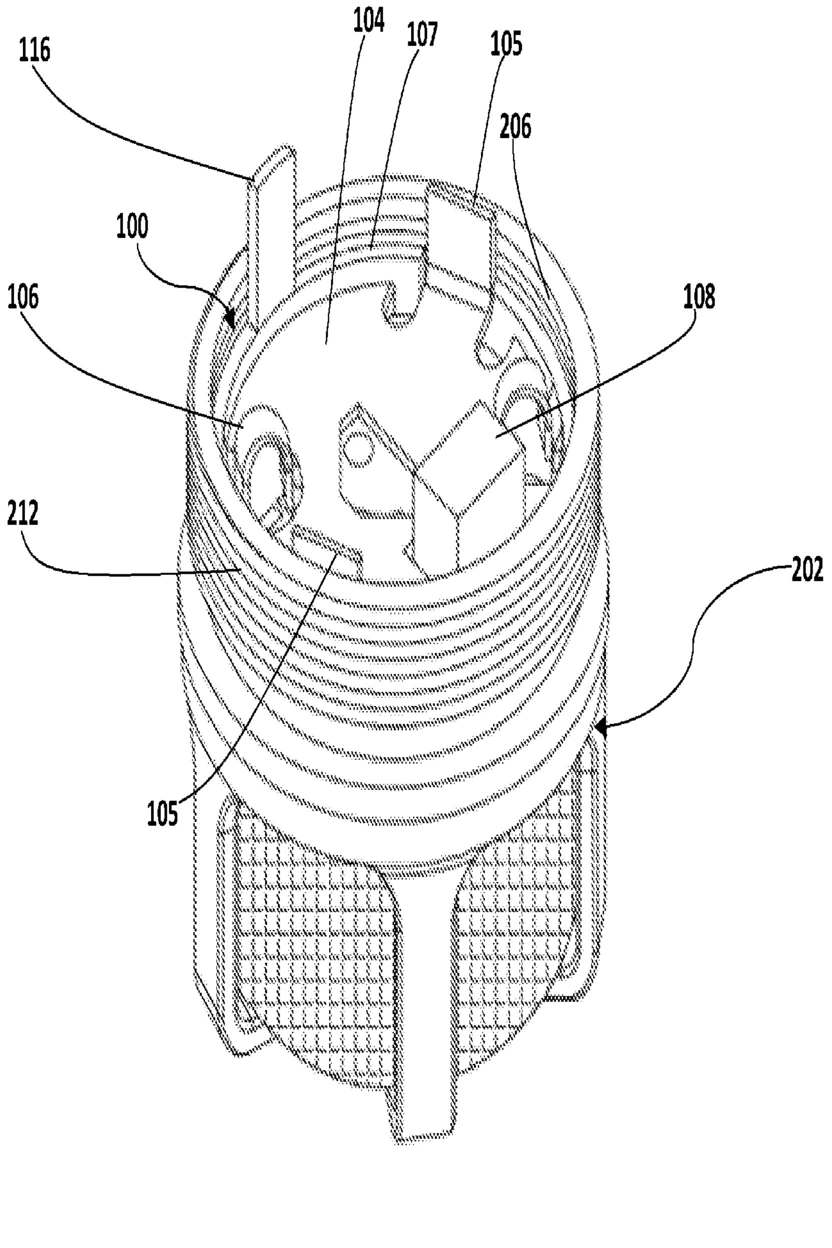
FIG. 2 exemplarily illustrates a perspective view of a replaceable module positioned in a lower enclosure of the gas detector, according to one or more embodiments of the disclosure.

FIG. 1 exemplarily illustrates a cross-sectional view of a gas detector 200 according to one or more embodiments of the disclosure. FIG. 2 exemplarily illustrates a perspective view of a replaceable module 100 positioned in a lower enclosure 202 of the gas detector 200 according to one or more embodiments of the disclosure. Referring to FIG. 1 and FIG. 2, the gas detector 200 may be adapted to detect the presence of a hazardous gas in an area. Further, the gas detector 200 may be adapted to generate a trigger signal to indicate the presence of the hazardous gas. In an embodiment, the hazardous gas may include, but is not limited to, an oxide of Carbon, an oxide of Sulphur, an oxide of Nitrogen, a Polycyclic Aromatic Hydrocarbon, and an Aldehyde. The gas detector 200 may include the replaceable module 100, the lower enclosure 202, and an upper enclosure 204 adapted to be threadedly engaged with the lower enclosure 202.

The upper enclosure 204 may include a plurality of internal threads 210 formed on a portion of an internal periphery of the upper enclosure 204. Further, the lower enclosure 202 may include a plurality of external threads 212 formed on a portion of an external periphery of the lower enclosure 202. The plurality of external threads 212 of the lower enclosure 202 is adapted to be engaged with the plurality of internal threads 210 of the upper enclosure 204. The lower enclosure 202 may be adapted to accommodate the replaceable module 100. The upper enclosure 204 may include a second sensor circuit 208 adapted to be connected with the replaceable module 100. The upper enclosure 204 may include a receiving member (not shown) adapted to support the sensor housing 101. In an embodiment, the lower enclosure 202 and the upper enclosure 204 may be formed of a metallic material including, but not limited to, Stainless Steel and Aluminum.

The replaceable module 100 may include a sensor housing 101, a sensor 102, a first sensor circuit 103, and a cover 104 detachably connected to the sensor housing 101. The sensor housing 101, and the cover 104 detachably connected to the sensor housing 101, may collectively adapted to be snap fitted in the lower enclosure 202 of the gas detector 200. The replaceable module 100 may be removed periodically for repair, and then replaced. Further, in case of malfunctioning of the sensor 102, the replaceable module 100 may also be replaced. In an embodiment, the replaceable module 100 may be embodied as a consumable module, without departing from the scope of the disclosure.

Figure 3:
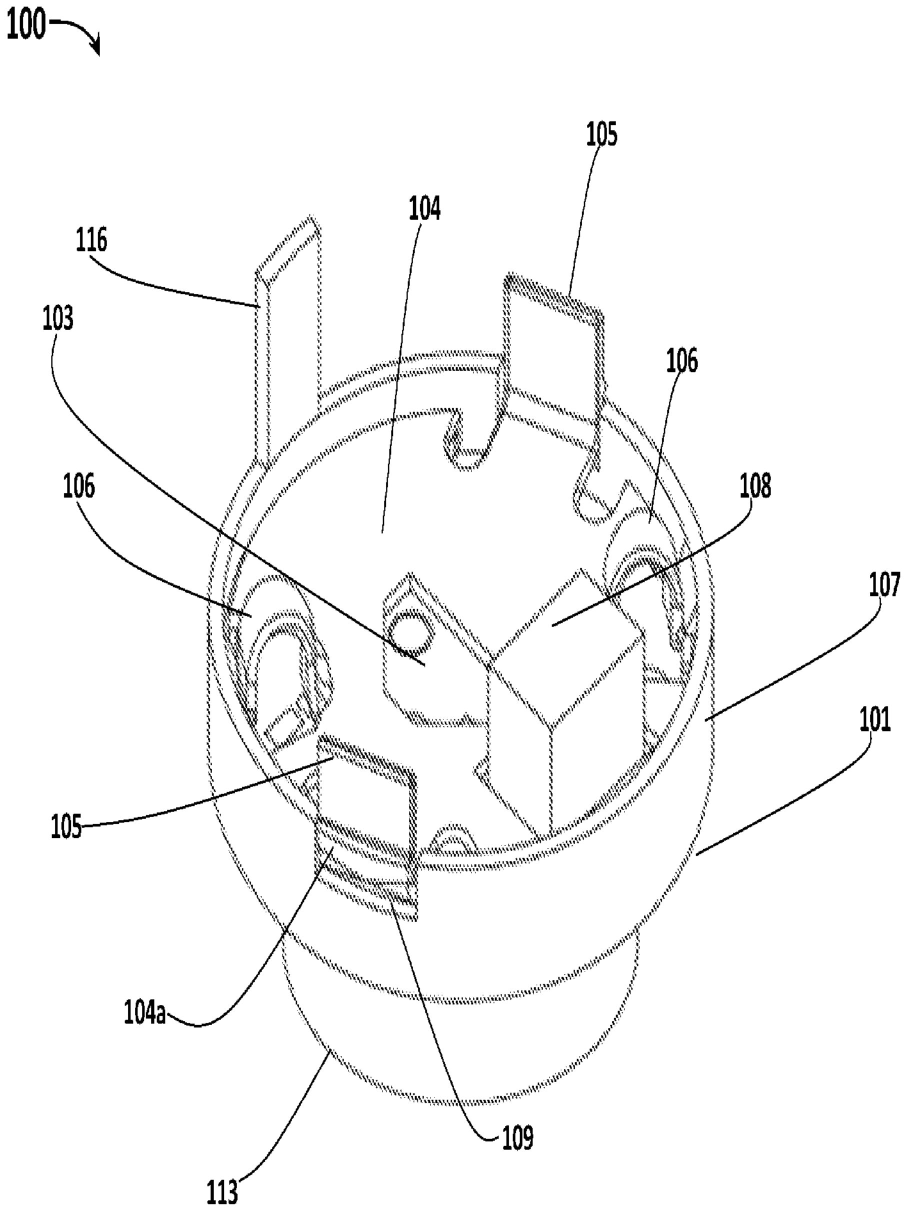
FIG. 3 exemplarily illustrates an isometric view of the replaceable module for the gas detector, according to one or more embodiments of the disclosure.
Figure 4:
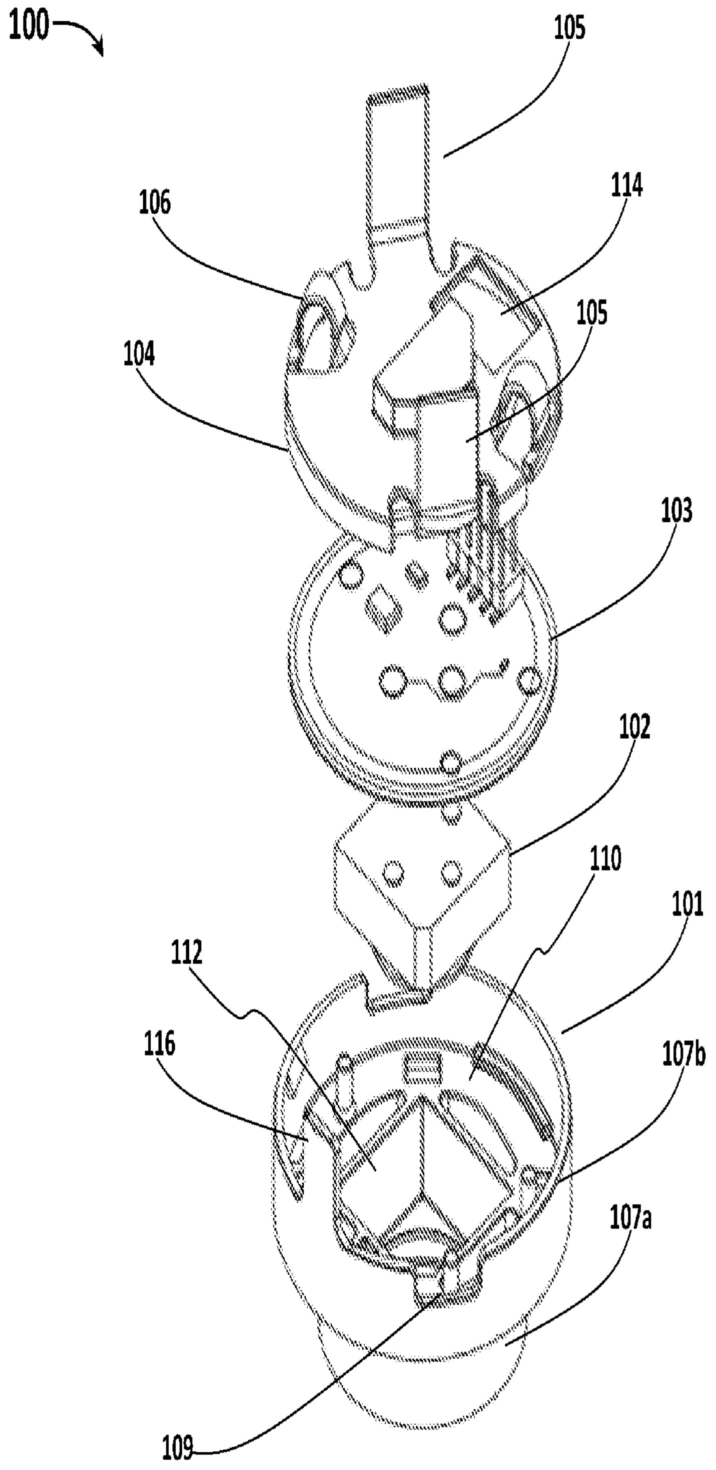
FIG. 4 exemplarily illustrates an exploded view of the replaceable module, according to one or more embodiments of the disclosure.

FIG. 3 exemplarily illustrates an isometric view of the replaceable module 100 for the gas detector 200 according to one or more embodiments of the disclosure. FIG. 4 exemplarily illustrates an exploded view of the replaceable module 100 according to one or more embodiments of the disclosure. Referring to FIG. 1, FIG. 2, FIG. 3 and FIG. 4, the replaceable module 100 is adapted to be installed in the lower enclosure 202 of the gas detector 200. The sensor housing 101 of the replaceable module 100 may be adapted to be disposed in the lower enclosure 202. The sensor housing 101 may include a base 113, a side wall 107 extending orthogonally from the base 113. The base 113 may adapted to form a surface contact with the lower enclosure 202 while the replaceable module 100 is installed in the lower enclosure 202.

Referring to FIG. 4, in an illustrated embodiment, the side wall 107 may include a first side wall 107*a* extending orthogonally from the base 113, and a second side wall 107*b* at an offset from the first side wall 107*a*. The base 113 and the first side wall 107*a* may be coupled to form a hollow portion 112 adapted to accommodate the sensor 102. The second side wall 107*b* of the sensor housing 101 defines a recess 110 adapted to accommodate the first sensor circuit 103 and the cover 104. The first side wall 107*a* and the second side wall 107*b* may individually be referred to as the side wall 107, without departing from the scope of the disclosure.

The side wall 107 may be adapted to accommodate the sensor 102, the first sensor circuit 103 and the cover 104. Further, the side wall 107 may define at least one cut-out 109 adapted to at least partially accommodate at least one resilient engaging member 105 of the cover 104, when the cover 104 is detachably coupled to the sensor housing 101. The at least one cut-out 109 may be a single continuous cut-out formed on the side wall 107. In another embodiment, the side wall 107 may define a plurality of cut-outs 109. Each of the plurality of cut-outs 109 may be located at intermittent locations along the side wall 107. In such an embodiment, each of the plurality of cut-outs may be equidistant to each other. Each of the plurality of cut-outs 109 is adapted to at least partially accommodate at least one resilient engaging member 105 of the cover 104, when the cover 104 is detachably coupled to the sensor housing 101.

In the illustrated embodiment, the plurality of cut-outs 109 may include two cut-outs. In another embodiment, the plurality of cut-outs 109 may include more than two cut-outs, without departing from the scope of the disclosure. In one embodiment, the sensor housing 101 may be formed of a polymeric material including, but not limited to, Polyphthalamide (PPA), polypropylene (PP), and nylon. In another embodiment, the sensor housing 101 may be formed of an elastomeric material including, but not limited to, rubber, Ethylene Propylene Diene (EPDM), Fluorocarbon (FKM) and silicone.

Further, the sensor housing 101 may include a protruding member 116 extending from the second side wall 107*b* in a parallel orientation relative to the second side wall 107*b*. The protruding member 116 is adapted to be engaged with the receiving member of the upper enclosure 204. The engagement of the protruding member 116 and the receiving member may form an interlocked connection. This interlocking of the protruding member 116 and the receiving member may restrict the rotation of the replaceable module 100 along with the upper enclosure 204.

The sensor 102 may be disposed in the hollow portion 112. The sensor 102 may be adapted to detect a presence of the hazardous gas. Alternatively, the sensor 102 may be calibrated to generate a trigger signal if a quantity of the hazardous gas exceeds a threshold level. In an embodiment, the sensor 102 may include, but is not limited to, combustible gas sensors, photoionization sensors, infrared point sensors, ultrasonic sensors, electrochemical gas sensors, and metal-oxide-semiconductor (MOS) sensors. The first sensor circuit 103 may be installed adjacent to the sensor 102, in the recess 110 of the sensor housing 101. In the illustrated embodiment, the first sensor circuit 103 may be installed, above the sensor 102, in the recess 110 of the sensor housing 101.

The first sensor circuit 103 is adapted to form an electrical connection with the second sensor circuit 208 of the upper enclosure 204. The first sensor circuit 103 may include, but is not limited to, a Printed Circuit Board (PCB) 108 positioned on the first sensor circuit 103. The PCB 108 is adapted to electrically connect to the second sensor circuit 208 positioned in the upper enclosure 204, while the lower enclosure 202 is threadedly engaged with the upper enclosure 204.

One of the first sensor circuit 103 and the second sensor circuit 208 may be construed to encompass one or a combination of microprocessors, suitable logic, circuits, audio interfaces, visual interfaces, haptic interfaces, or the like. The first sensor circuit 103 may include, but is not limited to, a microcontroller, a Reduced Instruction Set Computing (RISC) processor, an Application-Specific Integrated Circuit (ASIC) processor, a Complex Instruction Set Computing (CISC) processor, a central processing unit (CPU), a graphics processing unit (GPU), a state machine, and/or other processing units or circuits.

In an exemplary embodiment, the first sensor circuit 103 and/or the second sensor circuit 208 may receive power from a suitably coupled power source (not shown). For example, a battery or a power source may be electrically coupled to supply electrical power to the first sensor circuit 103 and/or the second sensor circuit 208. In an embodiment, the power source may be, for example, a battery, such as a rechargeable battery or a non-rechargeable battery. Examples of suitable batteries include, for example, a lithium battery (such as a lithium-ion battery), a nickel battery (such as a nickel-cadmium battery), and an alkaline battery.

The cover 104 may be detachably disposed in the sensor housing 101. The cover 104 is adapted to hold the first sensor circuit 103 in the recess 110 defined within the sensor housing 101. The cover 104 may include a plurality of snaps 106 positioned in proximity to the side wall 107 of the sensor housing 101. The plurality of snaps 106 may be adapted to be pulled for removing the cover 104 from the sensor housing 101. Further, the plurality of snaps 106 is adapted to hold the first sensor circuit 103 in the sensor housing 101 by securing the connection of the first sensor circuit 103 with the sensor 102. The plurality of snaps 106 may be pressed towards a center of the replaceable module 100 to remove the cover 104 from the sensor housing 101.

In one embodiment, the cover 104 may be formed of a polymeric material including, but not limited to, polyphthalamide (PPA), polypropylene (PP), and nylon. In another embodiment, the cover 104 may be formed of an elastomeric material including, but not limited to, rubber, Ethylene Propylene Diene (EPDM), Fluorocarbon (FKM) and silicone. Further, the PCB 108 of the first sensor circuit 103 is supported in the cover 104. The cover 104 may include an opening 114 adapted to support a portion of the PCB 108. The opening 114 may have a shape identical to the shape of the PCB 108, such that the PCB 108 may be secured in the opening 114 of the cover 104. Herein, the PCB 108 is adapted to form the electrical connection with the second sensor circuit 208 positioned in the upper enclosure 204.

Figure 5:
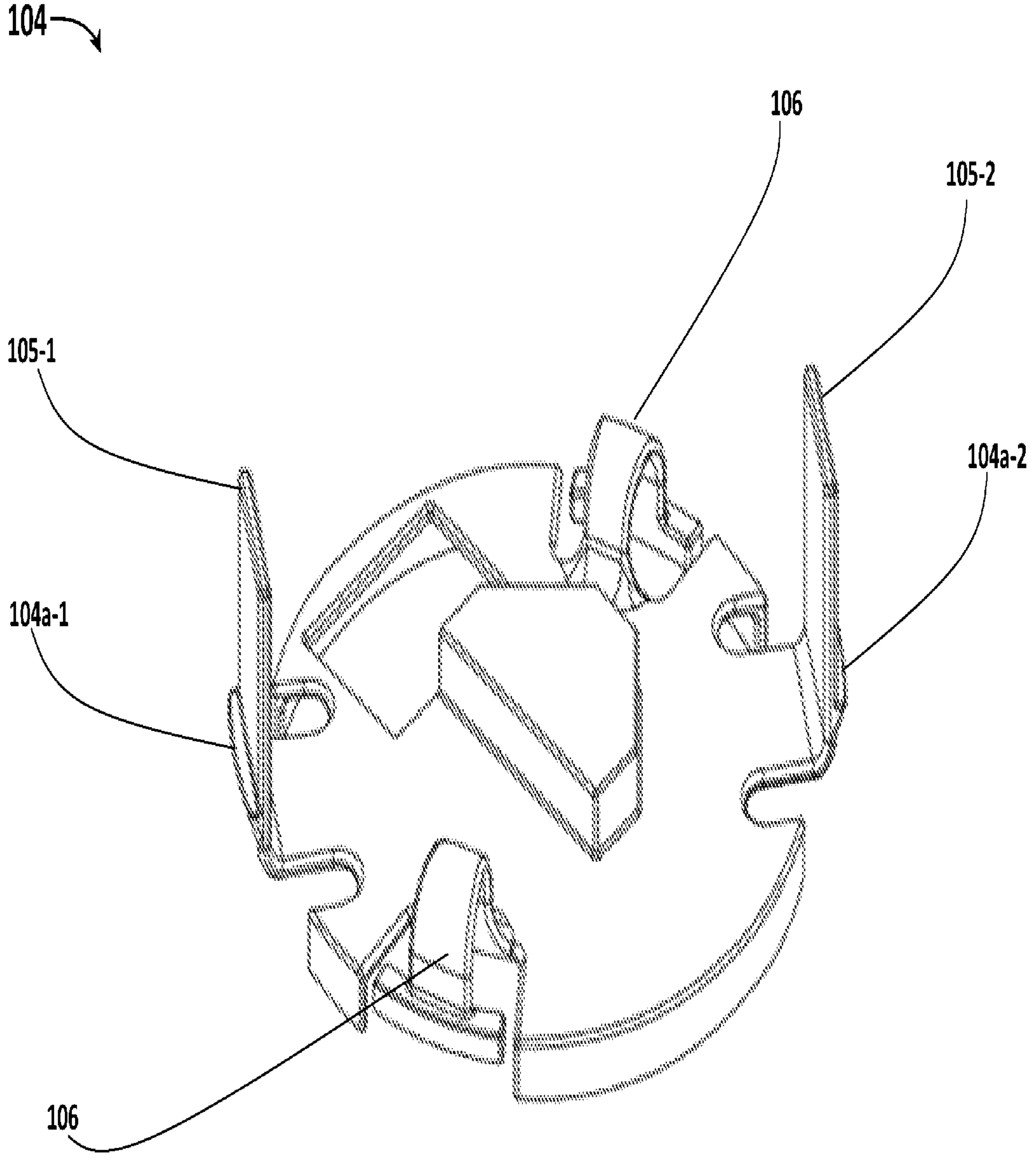
FIG. 5 exemplarily illustrates an isometric view of a cover of the replaceable module, according to one or more embodiments of the disclosure.

FIG. 5 exemplarily illustrates an isometric view of a cover 104 of the replaceable module 100 according to one or more embodiments of the disclosure. Referring to FIG. 1, FIG. 2, and FIG. 5, the cover 104 may include the at least one resilient engaging member 105 extending in an orthogonal orientation relative to the cover 104. The at least one resilient engaging member 105 may define at least one protrusion **104*a* extending in a parallel orientation relative to the cover 104. The at least one protrusion 104*a* may be adapted to engage with the lower enclosure 202 to restrict a movement of the cover 104 relative to the lower enclosure 202**.

As shown in FIG. 5, in illustrated embodiment, the at least one resilient engaging member 105 may include a first resilient engaging member 105-1 and a second resilient engaging member 105-2. Each of the first resilient engaging member 105-1 and the second resilient engaging member 105-2 may extend in the orthogonal orientation relative to the cover 104. Further, the first resilient engaging member 105-1 may define a first protrusion **104*a*-1 and the second resilient engaging member 105-2 may define a second protrusion 104*a*-2. The first protrusion 104*a*-1 and the second protrusion 104*a*-2 may extend in the parallel orientation relative to the cover 104**.

For the sake of readability, the first and the second resilient engaging members 105-1, 105-2 may hereinafter interchangeably be referred to as the resilient engaging members 105-1, 105-2. Further, the resilient engaging members 105 may individually be referred to as the at least one resilient engaging member 105, without departing from the scope of the disclosure. Also, the first protrusion **104*a*-1 and the second protrusion 104*a*-2 may hereinafter individually be referred to as the protrusions 104*a*-1, 104*a*-2. Moreover, the protrusions 104*a*-1, 104*a*-2 may individually be referred to as the at least one at least one protrusion 104*a*, without departing from the scope of the disclosure. In one or more embodiments, the cover 104 may include more than two resilient engaging members 105-1, 105-2 extending in the orthogonal orientation relative to the cover 104. Each of the resilient engaging members 105-1, 105-2 may define the at least one protrusion 104*a* extending in the parallel orientation relative to the cover 104**.

The at least one protrusion **104*a* is adapted to engage with an internal peripheral surface 206 of the lower enclosure 202 to restrict a movement of the cover 104 relative to the lower enclosure 202. Further, the engagement of the at least one protrusion 104*a* with the internal peripheral surface 206 may also restrict upward movement of the replaceable module 100 from the lower enclosure 202. In an embodiment, the at least one protrusion 104*a* may be adapted to be engaged with a mounting portion formed on the internal peripheral surface 206 of the lower enclosure 202 to retain the replaceable module 100 in the lower enclosure 202**.

The engagement of the at least one protrusion **104*a* with the internal peripheral surface 206 of the lower enclosure 202 may cause snap fitting of the replaceable module 100 in the lower enclosure 202. Further, the resilient engaging members 105-1, 105-2 are adapted to be pressed, inwardly, towards a center of the cover 104 to disengage the protrusions 104*a*-1, 104*a*-2 from the internal peripheral surface 206 of the lower enclosure 202. The disengagement of the protrusions 104*a*-1, 104*a*-2 from the internal peripheral surface 206 may allow removal of the replaceable module 100 from the lower enclosure 202**.

The at least one resilient engaging member 105 may be vertically extended from the cover 104 to provide a gripping area for inwardly pressing the at least one resilient engaging member. In an embodiment, the at least one resilient engaging member 105 may include a top portion and a bottom portion opposite to the top portion. The bottom portion may define the at least one protrusion **104*a* extending in the parallel orientation relative to the cover 104. Further, the top portion may define the gripping area adapted to press the at least one resilient engaging member 105. Thus, a user may grip the at least one resilient engaging member 105 and press inwardly towards the center of the cover 104 to disengage the at least one protrusion 104***a* from the internal peripheral surface 206. The at least one resilient engaging member 105 are easily accessible, even if the user is wearing gloves.

The replaceable module 100 may rotate with the lower enclosure 202 while the lower enclosure 202 is threadedly engaging with the upper enclosure 204. Further, the rotation of the replaceable module 100 with the upper enclosure 204 is restricted upon the interlocking of the protruding member 116 with the receiving member of the upper enclosure 204. Thus, the replaceable module 100 is restricted from rotation along with the rotation of the lower enclosure 202. Herein, the first sensor circuit 103 may also form the electrical connection with the second sensor circuit 208.

Figure 6:
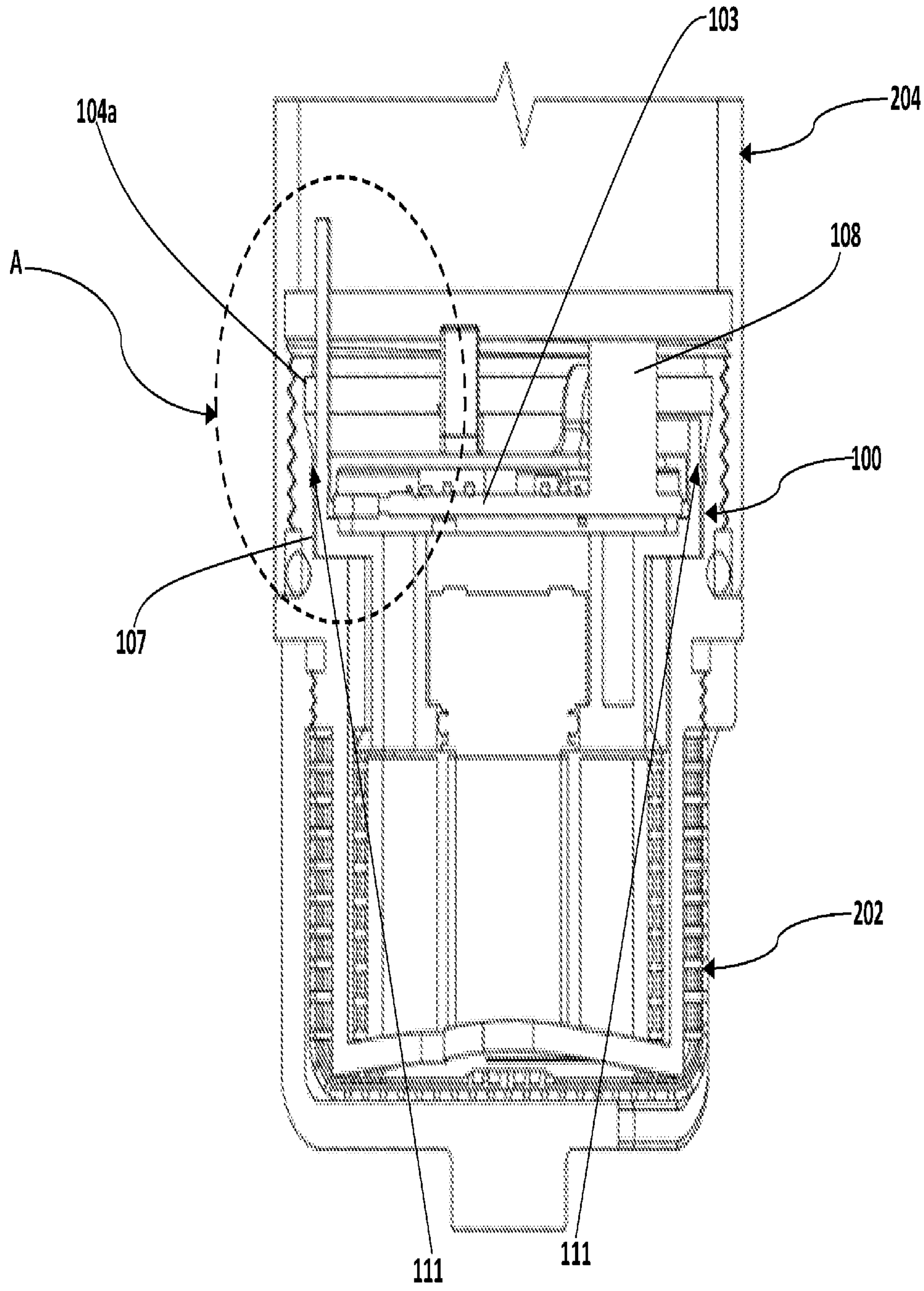
FIG. 6 exemplarily illustrates a partial cross-sectional view of the gas detector depicting a sealing member of the replaceable module, according to one or more embodiments of the disclosure.
Figure 7:
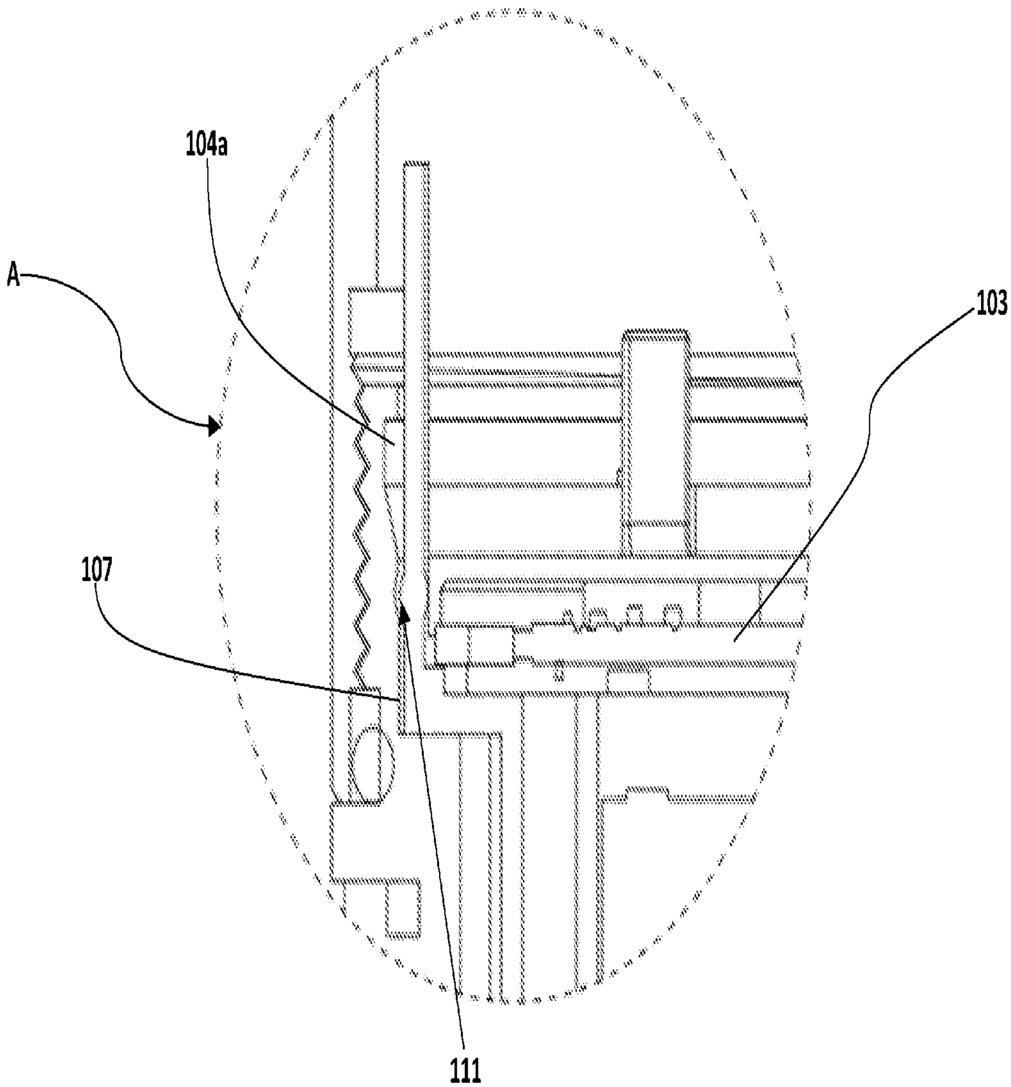
FIG. 7 exemplarily illustrates an enlarged view of a portion 'A' of the sealing member, according to one or more embodiments of the disclosure.

FIG. 6 exemplarily illustrates a partial cross-sectional view of a sealing member 111 of the replaceable module 100 for the gas detector 200 according to one or more embodiments of the disclosure. FIG. 7 exemplarily illustrates a cross-sectional view of a portion 'A' of the sealing member 111 according to one or more embodiments of the disclosure. Referring to FIG. 6 and FIG. 7, the replaceable module 100 may include the sealing member 111 protruding from the side wall 107 as shown in portion 'A'. In the illustrated embodiment, the sealing member 111 may be protruded outwardly from the side wall 107 of the sensor housing 101. The sealing member 111 may be adapted to form a sealing surface in contact with the internal peripheral surface 206 of the lower enclosure 202 to prevent ingress of foreign particles into the lower enclosure 202. The foreign particles may include, but is not limited to, dust and water, without departing from the scope of the disclosure.

The sealing member 111 may form an interference fit with the internal peripheral surface 206 of the lower enclosure 202 to form the sealed surface with the lower enclosure 202. The sealing member 111 may be an integral part of the sensor housing 101 of the replaceable module 100. The sealing member 111 and the sensor housing 101 may be formed of a same material. In one embodiment, the sealing member 111 may be formed of a polymeric material. In another embodiment, the sealing member 111 may be formed of an elastomeric material. In one embodiment, the sensor housing 101 and the sealing member 111 may be integrally formed using an injection molding process. In another embodiment, the sensor housing 101 and the sealing member 111 may be integrally formed using a 3-D printing process.

The sealing member 111 may be integrated with the sensor housing 101. The sealing member 111 of the replaceable module 100 itself may be shaped such that the sealing member 111 may prevent ingress of foreign particles. This eliminates the use of the O-rings and/or gaskets in the replaceable module 100 as the sealing member 111 is an integral part of the replaceable module 100.

The implementation of existing O-rings and gaskets not only increases the number of components, but also introduces additional inspection steps during an assembly of the consumable sensor module. Further, effective sealing cannot be achieved if O-rings and gaskets are not seated properly in the consumable sensor module. However, the sealing member 111 eliminates the implementation of separate O-rings and/or gaskets, so that the number of components of the replaceable module 100 is substantially reduced.

Further, the number of steps for assembling the replaceable module 100 are also reduced as the sealing member 111 is integrally formed with the sensor housing 101 of the replaceable module 100. This reduces the time associated with the assembly of the replaceable module 100. Also, the sealing member 111 may eliminate the risk of the O-ring or gasket not being seated correctly when the replaceable module 100 is assembled. Moreover, the serviceability of the replaceable module 100 is also improved as a requirement of periodic inspection and/or replacement of O-ring or gasket in the replaceable module 100 is eliminated.

Figure 8A:
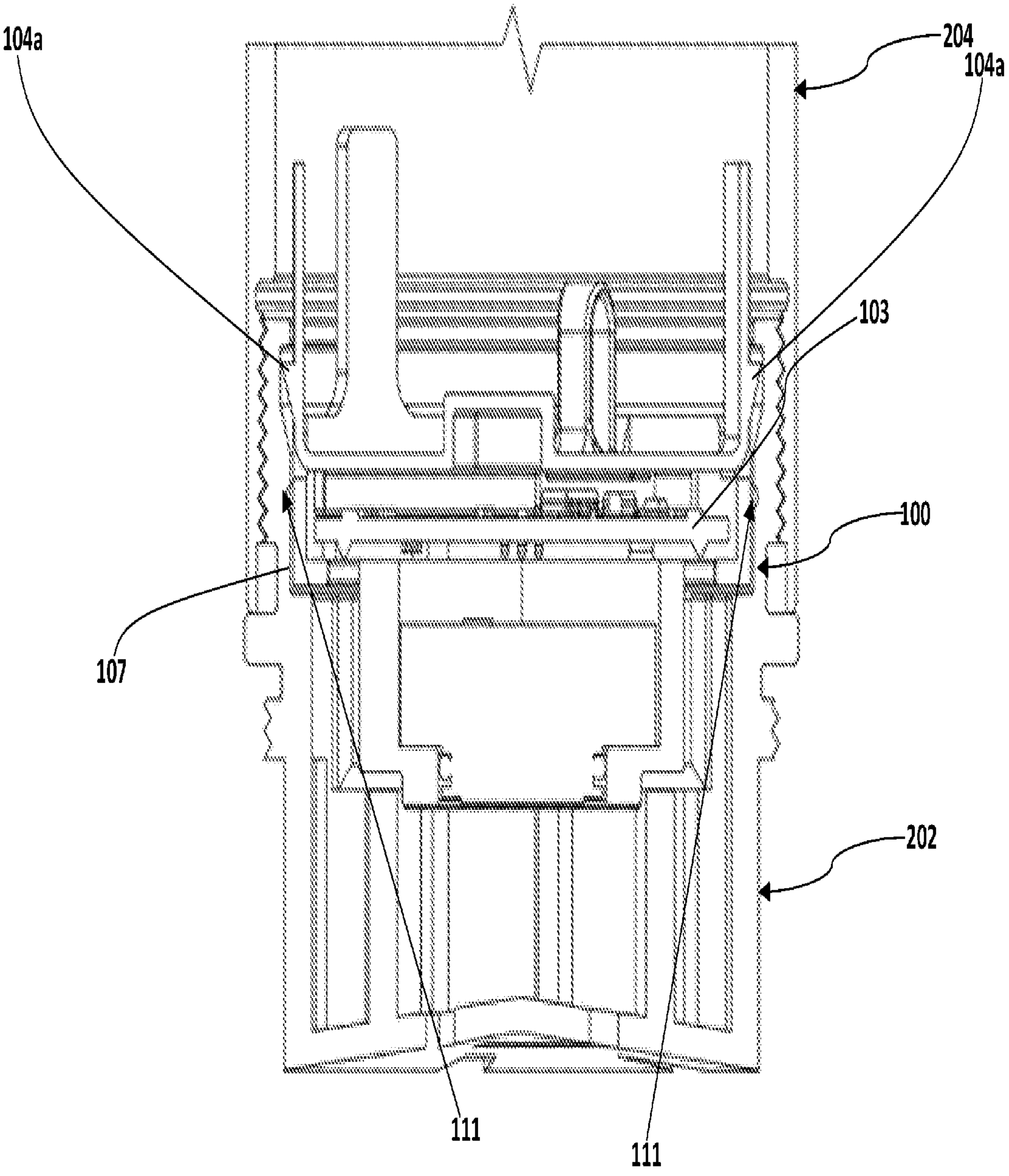
FIG. 8A exemplarily illustrates another partial cross-sectional view of the gas detector depicting the sealing member of the replaceable module, according to one or more embodiments of the disclosure.
Figure 8B:
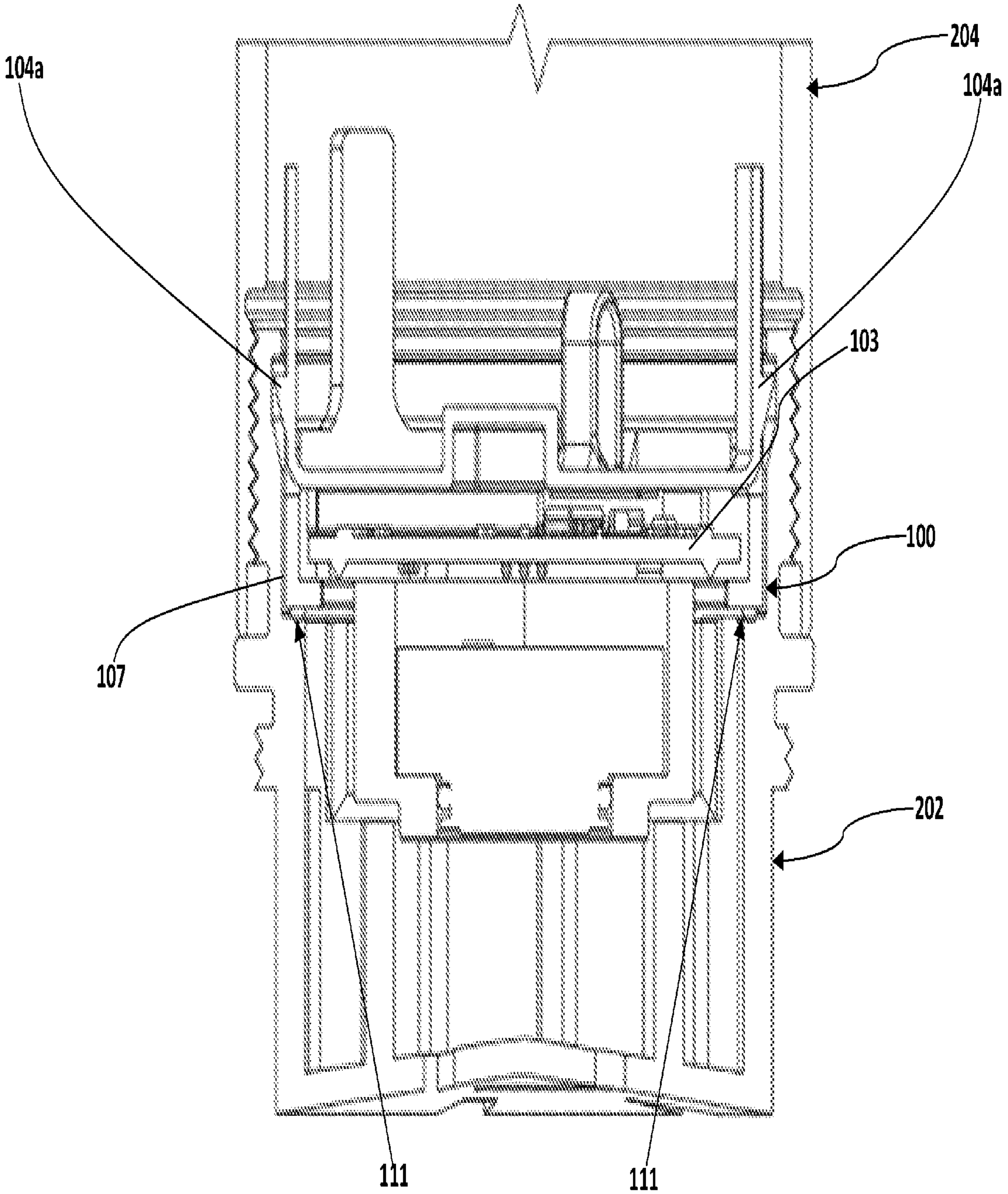
FIG. 8B exemplarily illustrates another partial cross-sectional view of the gas detector depicting the sealing member of the replaceable module, according to one or more embodiments of the disclosure.

FIG. 8A exemplarily illustrates another partial cross-sectional view of the gas detector 200 depicting the sealing member 111 of the replaceable module 100, according to one or more embodiments of the disclosure. FIG. 8B exemplarily illustrates another partial cross-sectional view of the gas detector 200 depicting the sealing member 111 of the replaceable module 100. Herein, the sealing member 111 may protrude outwardly from the recess 110 of the sensor housing 101. The sealing member 111 may form the sealing surface in contact with the internal peripheral surface 206 of the lower enclosure 202 to prevent ingress of foreign particles into the lower enclosure 202.

Figure 9:
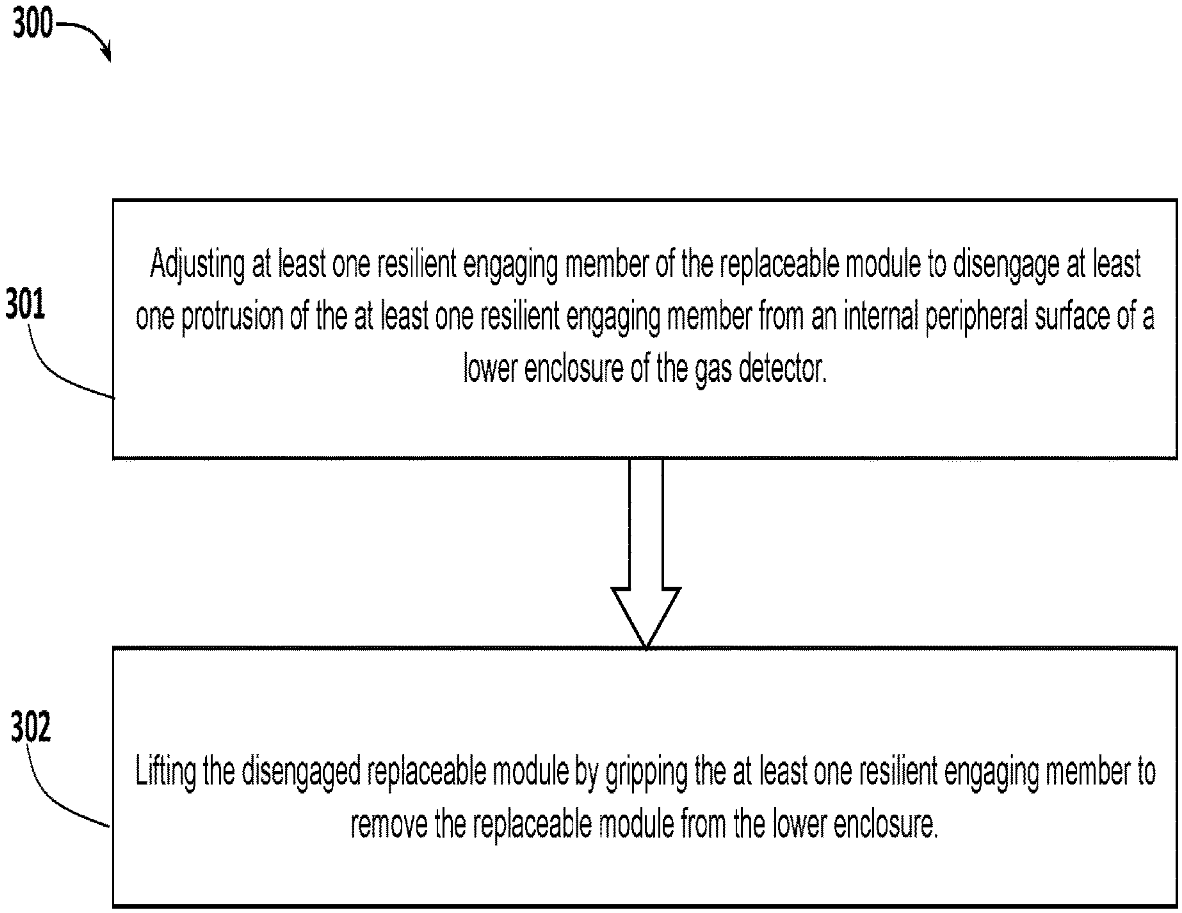
FIG. 9 exemplarily illustrates a flowchart depicting a method of replacing the replaceable module of the gas detector, according to one or more embodiments of the disclosure.

FIG. 9 exemplarily illustrates a flowchart depicting a method 300 of replacing the replaceable module 100 of the gas detector 200, according to one or more embodiments of the disclosure.

At a first step 301, the method 300 may include adjusting the at least one resilient engaging member 105 to disengage the at least one protrusion 104*a* of the at least one resilient engaging member 105 from the internal peripheral surface 206 of the lower enclosure 202. The at least one resilient engaging member 105 may be adjusted by pressing the at least one resilient engaging member 105 inwardly to disengage the at least one protrusion 104*a* from the mounting portion of the internal peripheral surface 206.

The at least one resilient engaging member 105 may be pressed, inwardly, towards the center of the cover 104. Upon the pressing of the at least one resilient engaging member 105, the at least one protrusion 104*a* may be moved away from the internal peripheral surface 206 and disengaged. In an embodiment, the at least one protrusion 104*a* may be disengaged from the mounting portion formed on the internal peripheral surface 206 of the lower enclosure 202, upon inward pressing of the at least one resilient engaging member 105.

At the second step 302, the method 300 may include lifting the disengaged replaceable module 100 by gripping the at least one resilient engaging member 105 to remove the replaceable module 100 from the lower enclosure 202. Herein, the at least one protrusion 104*a* may be already disengaged from the internal peripheral surface 206, so that the user may grip the at least one resilient engaging member 105 and lift the disengaged replaceable module 100 from the lower enclosure 202. In this way, the disengaged replaceable module 100 may be removed from the lower enclosure 202. The replaceable module 100 may be replaced without using any lifting tool and untightening of mechanical fasteners. Thus, the method 300 is convenient for the user as the method 300 consumes less time and effort for replacing the replaceable module 100 from the lower enclosure 202.

After removing the replaceable module 100 from the lower enclosure 202, another replaceable module may be installed in the lower enclosure 202. Another replaceable module may be similar to the replaceable module 100. For the sake of readability, another replaceable module may be referred to as the replaceable module 100, without departing from the scope of the disclosure. For installing the replaceable module 100 in the lower enclosure 202, the replaceable module 100 may be positioned in the lower enclosure 202. Further, a vertical force may be applied on the cover 104 of the replaceable module 100 to push the replaceable module 100 toward the lower enclosure 202. Upon applying the force, the at least one protrusion 104*a* of the replaceable module 100 may engage with the internal peripheral surface 206 of the lower enclosure 202. The installation of the replaceable module 100 may be done without any mechanical fasteners and/or one or more tools. Herein, only the engagement of the at least one protrusion 104*a* with the internal peripheral surface 206 of the lower enclosure 202, is responsible to snap fit the replaceable module 100 in the lower enclosure 202. Thus, the installation time and effort are reduced which further reduces a cost associated with the installation of the replaceable module 100.

As would be gathered, the disclosure offers the replaceable module 100 for the gas detector 200. The replaceable module 100 is adapted to be snap fit in the lower enclosure 202 of the gas detector 200, which reduces the risk of damaging the replaceable module 100 due to the replaceable module 100 falling out of the lower enclosure 202. During the disengagement of the lower enclosure 202 and the upper enclosure 204, initially, the PCB 108 disengages from the second sensor circuit 208 of the upper enclosure 204. Thus, the lower enclosure 202 may be unthreaded to disengage from the upper enclosure 204 with an inherent disconnection and/or damage of the PCB 108.

Further, the installation of the replaceable module 100 is only supported by the engagement of the at least one protrusion 104*a*, so the replaceable module 100 may be installed without using any additional parts. Thus, the number of parts of the replaceable module 100 is reduced, which further reduces the installation cost. Moreover, the replacement of the replaceable module 100 is easier for the user since the user may disengage and remove the replaceable module 100 from the lower enclosure 202 without using one or more tools. This results in quick and simple replacement of the replaceable module 100, while reducing the time and the cost associated with such replacement. Also, the sealing member of the replaceable module 100 may eliminate the implementation of separate O-rings and/or gaskets. Thus, the number of components of the replaceable module 100 and the number of steps for assembling also are reduced.

Therefore, the replaceable module 100 of the disclosure is cost-effective and more convenient to install and/or replace which consumes less time consuming and effort. Further, the method 300 of replacing the replaceable module 100 of the disclosure is cost-effective and convenient to implement.

While specific language has been used to describe the subject matter, any limitations arising on account thereto, are not intended. As would be apparent to a person in the art, various working modifications may be made to the method 300 in order to implement the inventive concept as taught herein. The drawings and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment.

What is claimed is:

1. A gas detector comprising:
- a replaceable module comprising:
  - a sensor housing adapted to accommodate a sensor and a first sensor circuit of the gas detector, wherein the sensor is detachably connected to the first sensor circuit; and
  - a cover detachably connected to the sensor housing, the cover comprising at least one resilient engaging member extending from the cover and defines at least one protrusion;
- a lower enclosure of the gas detector configured to restrict a movement of the cover relative to the lower enclosure, the at least one protrusion configured to engage the lower enclosure;
- an upper enclosure configured to engage the lower enclosure.

2. The gas detector of claim 1, wherein the sensor housing and the cover detachably connected to the sensor housing are collectively adapted to be snap fit in the lower enclosure of the gas detector.

3. The gas detector of claim 1, wherein the at least one protrusion is extended in a parallel orientation relative to the cover, the at least one protrusion is adapted to engage with an internal peripheral surface of the lower enclosure to restrict an upward movement of the replaceable module from the lower enclosure.

4. The gas detector of claim 3, wherein the at least one protrusion is adapted to be engaged with a mounting portion formed on the internal peripheral surface of the lower enclosure.

5. The gas detector of claim 3, wherein the at least one resilient engaging member is extended in an orthogonal orientation relative to the cover, the at least one resilient engaging member is adapted to be pressed towards to a center of the cover to disengage the at least one protrusion from the internal peripheral surface of the lower enclosure to remove the replaceable module from the lower enclosure.

6. The gas detector of claim 1, wherein the at least one resilient engaging member is adapted to be pressed to disengage the at least one protrusion from the lower enclosure to remove the replaceable module from the lower enclosure.

7. The gas detector of claim 1, wherein the sensor housing comprises a side wall defining at least one cut-out adapted to at least partially accommodate the at least one resilient engaging member, when the cover is detachably coupled to the sensor housing.

8. The gas detector of claim 1, wherein the at least one resilient engaging member is vertically extended from the cover to provide a gripping area for inwardly pressing the at least one resilient engaging member.

9. The gas detector of claim 1, wherein the cover is disposed in the sensor housing to hold the first sensor circuit in a recess defined within the sensor housing.

10. The gas detector of claim 1, wherein the cover comprises a plurality of snaps positioned in proximity to a side wall of the sensor housing, wherein the plurality of snaps is adapted to be pressed towards a center of the replaceable module to remove the cover from the sensor housing.

11. The gas detector of claim 1, wherein each of the sensor housing and the cover is formed of at least one of a polymeric material and an elastomeric material.

12. A replaceable module for a gas detector, the replaceable module comprising:
- a sensor housing adapted to accommodate a sensor and a first sensor circuit of the gas detector, wherein the sensor is detachably connected to the first sensor circuit; and
- a cover detachably connected to the sensor housing, the cover comprising at least one resilient engaging member extending from the cover and defines at least one protrusion adapted to engage with a lower enclosure of the gas detector to restrict a movement of the cover relative to the lower enclosure;

wherein the first sensor circuit is installed in the sensor housing positioned in the lower enclosure and is adapted to form an electrical connection with a second sensor circuit of the upper enclosure of the gas detector adapted to be engaged with the lower enclosure.

13. The replaceable module of claim 12, wherein the sensor housing comprises a protruding member adapted to interlock with a receiving member of the upper enclosure to restrict rotation of the replaceable module with the upper enclosure.

14. The replaceable module of claim 12, wherein a PCB is supported in the cover, and the PCB is adapted to form the electrical connection with the second sensor circuit positioned in the upper enclosure.

15. A gas detector comprising:

a replaceable module comprising:

a sensor housing adapted to accommodate a sensor and a first sensor circuit of the gas detector, the sensor is detachably connected to the first sensor circuit, wherein the sensor housing comprises:

a side wall; and a sealing member protruding from the side wall, wherein the sealing member is adapted to form a sealing surface in contact with an internal peripheral surface of the lower enclosure; and a cover detachably connected to the sensor housing, the cover comprising at least one resilient engaging member extending from the cover and defines at least one protrusion;

a lower enclosure of the gas detector to restrict a movement of the cover relative to the lower enclosure, the at least one protrusion configured to engage the lower enclosure;

an upper enclosure configured to engage the lower enclosure.

16. The gas detector of claim 15, wherein the sensor housing and the cover detachably connected to the sensor housing are collectively adapted to be snap fit in the lower enclosure of the gas detector.

17. The gas detector of claim 15, wherein the sealing member is adapted to form an interference fit with the internal peripheral surface of the lower enclosure to form the sealing surface with the lower enclosure.

18. The gas detector of claim 15, wherein the sealing member is integrated with the sensor housing of the replaceable module, wherein the sensor housing and the sealing member are integrally formed.

* * * * *